US012747518B2

(12) United States Patent
Mizumura et al.

(10) Patent No.: US 12,747,518 B2
(45) Date of Patent: Sep. 29, 2026

(54) COLORED FIBER, METHOD FOR MANUFACTURING COLORED FIBER, AND FIBER PRODUCT

(71) Applicant: KANEKA CORPORATION, Osaka (JP)

(72) Inventors: Masatoshi Mizumura, Kanagawa (JP); Akihiro Okamoto, Hyogo (JP); Takeshi Tanaka, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 202 days.

(21) Appl. No.: 18/891,149

(22) Filed: Sep. 20, 2024

(65) Prior Publication Data

US 2025/0027232 A1 Jan. 23, 2025

Related U.S. Application Data

(63) Continuation of application No. PCT/JP2023/010705, filed on Mar. 17, 2023.

(30) Foreign Application Priority Data

Mar. 23, 2022 (JP) ................................ 2022-047004

(51) Int. Cl.

| | |
|---|---|
| ***D06P 1/00*** | (2006.01) |
| ***A41G 3/00*** | (2006.01) |
| ***C07D 471/10*** | (2006.01) |
| ***C08K 5/3465*** | (2006.01) |
| ***C09B 31/153*** | (2006.01) |
| ***D01F 1/06*** | (2006.01) |
| ***D01F 6/40*** | (2006.01) |
| ***D06P 1/08*** | (2006.01) |

(52) U.S. Cl.

CPC ............ *D01F 1/06* (2013.01); *A41G 3/0083* (2013.01); *C07D 471/10* (2013.01); *C08K 5/3465* (2013.01); *C09B 31/153* (2013.01); *D01F 6/40* (2013.01); *D06P 1/08* (2013.01); *D10B 2503/08* (2013.01)

(58) Field of Classification Search

CPC ........... D01F 1/06; D01F 6/40; A41G 3/0083; C07D 471/10; C08K 5/3465; C09B 31/153; C09B 31/14; D06P 1/08; D06P 3/76; D10B 2503/08

USPC ........................................................... 8/669

See application file for complete search history.

(56) References Cited

U.S. PATENT DOCUMENTS

2019/0021425 A1 1/2019 Tanaka et al.
2021/0214560 A1* 7/2021 Fujie ..................... G03G 9/122

FOREIGN PATENT DOCUMENTS

WO 2017/164299 A1 9/2017
WO WO 2020067063 A1 * 4/2020 ................ D06P 1/04

OTHER PUBLICATIONS

STIC Search Report dated Jun. 2, 2026.*
International Search Report issued in corresponding International Application No. PCT/JP2023/010705 mailed Jun. 13, 2023 (5 pages).
Written Opinion issued in corresponding International Application No. PCT/JP2023/010705 mailed Jun. 13, 2023 (3 pages).

* cited by examiner

*Primary Examiner* — Eisa B Elhilo
(74) *Attorney, Agent, or Firm* — Osha Bergman Watanabe & Burton LLP

(57) ABSTRACT

A colored fiber excellent in heat generation suppression property and fastness is provided. A method for manufacturing a colored fiber, and a fiber product is also provided. The colored fiber includes a fiber and a compound expressed by Formula (1) below.

(1)

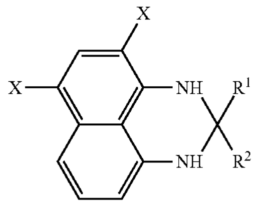

20 Claims, No Drawings

COLORED FIBER, METHOD FOR MANUFACTURING COLORED FIBER, AND FIBER PRODUCT

CROSS-REFERENCE TO RELATED APPLICATIONS

This application is a Continuation of PCT International Application No. PCT/JP2023/010705 filed on Mar. 17, 2023, which claims priority under 35 U.S.C. § 119(a) to Japanese Patent Application No. 2022-047004 filed on Mar. 23, 2022. The above applications are hereby expressly incorporated by reference, in their entirety, into the present application.

TECHNICAL FIELD

One or more embodiments of the present invention relate to a colored fiber, a method for manufacturing a colored fiber, and a fiber product.

BACKGROUND

Colored fibers are recently used in various fields. For example, Patent Literature 1 discloses "an acrylic fiber for artificial hair, including an acrylic polymer and a condensed phosphate, wherein the acrylic polymer contains 29.5 to 79.5 mass % of acrylonitrile, 20 to 70 mass % of vinyl chloride and/or vinylidene chloride, and 0.5 to 5 mass % of a sulfonate group-containing vinyl monomer with respect to a total mass of the acrylic polymer, and a content of the condensed phosphate in the acrylic fiber for artificial hair is 0.05 to 0.57 mass %" as an acrylic fiber for artificial hair.

In Patent Literature 1, carbon black is mainly used as a colorant.

PATENT LITERATURE

Patent Literature 1: WO 2017/164299 A

A colored fiber containing carbon black (particularly, black fiber) increases of the fiber surface temperature to a high temperature under a long-time exposure to sunlight. Therefore, in the case of applying a colored fiber containing carbon black to, for example, applications for hair (such as a wig), discomfort may be caused at the time of wearing due to the above, and there has been a demand for improvement.

That is, there has been a demand for providing a colored fiber (particularly, black fiber) having a fiber surface temperature that is less likely to increase to a high temperature even under a long-time exposure to sunlight (hereinafter, also referred to as "having an excellent heat generation suppression property").

Furthermore, colored fibers are also required to have basic performance, i.e., excellent fixability of a colorant to the fibers (hereinafter also referred to as "having excellent fastness").

SUMMARY

Accordingly, a colored fiber excellent in heat generation suppression property and fastness is provided.

One or more embodiments of the present invention is to provide a method for manufacturing a colored fiber, and a fiber product.

As a result of intensive studies on the above, the present inventors have found that the above can be addressed by the following configurations.

[1] A colored fiber comprising a fiber and a compound expressed by Formula (1) described below.

[2] The colored fiber according to [1], wherein the fiber is an acrylic fiber including an acrylic polymer.

[3] The colored fiber according to [2], wherein the acrylic polymer includes:

a repeating unit X derived from an acrylonitrile monomer;

one or more kinds of repeating units Y selected from the group consisting of repeating units derived from a vinylidene chloride monomer and repeating units derived from a vinyl chloride monomer; and a repeating unit Z derived from a sulfonate group-containing vinyl monomer, a content of the repeating unit X is 29.5 to 79.5 mass % with respect to a total mass of the acrylic polymer, a content of the repeating units Y is 20 to 70 mass % with respect to the total mass of the acrylic polymer, and a content of the repeating unit Z is 0.5 to 5 mass % with respect to the total mass of the acrylic polymer.

[4] The colored fiber according to any one of [1] to [3], wherein in Formula (1), at least one of $R^1$ or $R^2$ represents a substituent including a partial structure expressed by Formula (1b), or $R^1$ and $R^2$ are bonded to each other to form a ring and the ring includes a partial structure of $X_2^+$ $(Y^-)$.

[5] The colored fiber according to any one of [1] to [4], wherein the anionic counterion of $Y^-$ is one selected from the group consisting of sulfonimide ions, a hexafluorophosphate ion, an iodide ion, a saccharin ion, and a tosylate ion.

[6] A method for manufacturing the colored fiber according to any one of [1] to [5], the method comprising a step of wet-spinning a spinning dope containing a polymer included in the fiber and the compound expressed by Formula (1).

[7] A method for manufacturing the colored fiber according to any one of [1] to [5], the method comprising a step of dyeing the fiber using an aqueous solution containing the compound expressed by Formula (1).

[8] A fiber product comprising the colored fiber according to any one of [1] to [5].

[9] The fiber product according to [8], wherein the fiber product is a head decoration product.

[10] The fiber product according to [9], wherein the head decoration product is selected from the group consisting of fiber bundles for hair, weaving products, wigs, braids, toupees, hair extensions, and hair accessories.

According to one or more embodiments of the present invention, it is possible to provide a colored fiber excellent in heat generation suppression property and fastness.

Furthermore, according to one or more embodiments of the present invention, it is possible to provide a method for manufacturing a colored fiber, and a fiber product.

DETAILED DESCRIPTION

Hereinafter, one or more embodiments of the present invention will be described in detail.

The description of the constituent feature below may be made on the basis of a representative embodiment of the present disclosure, but the present disclosure is not limited to such an embodiment.

In the present disclosure, the term "organic group" refers to a group including at least one carbon atom. In the present disclosure, a numerical range represented using "to" means a range including numerical values described before and after "to" as a lower limit value and an upper limit value.

The bonding direction of a divalent group denoted in the present description is not particularly limited, and for example, in a case where L in X-L-Y represents —COO—, L may represent *1—O—CO—*2 or *1—CO—O—*2 in which the position bonded to the X side is represented by *1 and the position bonded to the Y side is represented by *2.

In the present disclosure, a (meth)acrylate represents an acrylate and a methacrylate, a (meth)acryl represents an acryl and a methacryl, and a (meth)acryloyl represents an acryloyl and a methacryloyl.

In the present disclosure, the weight average molecular weight (Mw) and the dispersion degree (also referred to as molecular weight distribution) (Mw/Mn) of a polymer are defined as polystyrene-equivalent values obtained by a gel permeation chromatography (GPC) apparatus.

Colored Fiber

The colored fiber of one or more embodiments of the present invention includes a fiber and a compound expressed by Formula (1) described below (hereinafter, also referred to as "specific colorant").

The colored fiber of one or more embodiments of the present invention having the above configuration has a fiber surface temperature that is less likely to increase to a high temperature even under a long-time exposure to sunlight (in other words, has an excellent heat generation suppression property). The fastness of the specific colorant to the fiber is also excellent.

Details of the action mechanism by which the colored fiber of one or more embodiments of the present invention exerts a desired effect are not clear, but the present inventors presume as follows.

Carbon black, which is a black colorant, has an absorption band in the visible light region and the infrared region, and therefore when carbon black is exposed to sunlight for a long time, the degree of heat generation is large. On the other hand, the specific colorant does not have an absorption band in the infrared region although the specific colorant is a black colorant, and therefore heat generation can be greatly suppressed as compared with carbon black.

Furthermore, the specific colorant has a cationic structural site in the molecule, and it is considered that the fixability to the fiber is secured due to this structure. As a result of the studies of the present inventors, it has been confirmed that the specific colorant exhibits excellent fixability particularly to synthetic fibers (among them, particularly to acrylic fibers such as modacrylic fibers).

Hereinafter, the colored fiber of one or more embodiments of the present invention will be described.

Hereinafter, the fact that the heat generation suppression property of the colored fiber is more excellent and/or the fact that the fastness of the specific colorant to the fiber is more excellent may be referred to as "an effect of one or more embodiments of the present invention being more excellent".

Compound Expressed by Formula (1) (Specific Colorant)

The colored fiber of one or more embodiments of the present invention includes the compound expressed by Formula (1) (specific colorant).

[Chemical Formula 1]

(1)

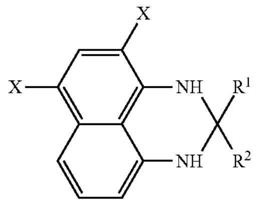

In Formula (1), $R^1$ and $R^2$ each independently represent a hydrogen atom or a substituent. $R^1$ and $R^2$ are optionally bonded to each other to form a ring. One of two Xs represents a hydrogen atom, and the other represents a group expressed by Formula (1a) described below.

[Chemical Formula 2]

(1a)

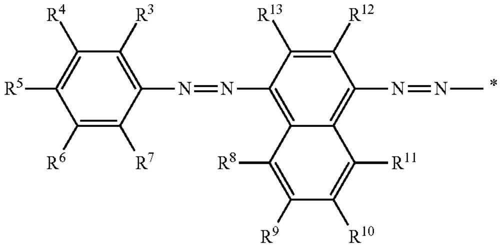

In Formula (1a), $R^3$ to $R^{13}$ each independently represent a hydrogen atom or a substituent. Two adjacent groups among $R^3$ to $R^{13}$ are optionally bonded to each other to form a ring. * represents a bonding position.

The compound expressed by Formula (1) satisfies at least one of Requirements 1 to 3 described below.

Requirement 1: at least one of $R^1$ to $R^{13}$ represents a substituent including a partial structure expressed by Formula (1b) described below.

$$*—X_1^+Y^-$$ Formula (1b):

In Formula (1b), $X_1^+$ represents a cationic group. $Y^-$ represents an anionic counterion. * represents a bonding position.

Requirement 2: $R^1$ and $R^2$ are bonded to each other to form a ring, and the ring includes a partial structure of $X_2^+$ ($Y^-$). $X_{2+}$ represents a cationic atom constituting a ring member atom of the ring. $Y^-$ represents an anionic counterion.

Requirement 3: two adjacent groups among $R^3$ to $R^{13}$ are bonded to each other to form a ring, and the ring includes a partial structure of $X_3^+$ ($Y^-$). $X_3^+$ represents a cationic atom constituting a ring member atom of the ring. $Y^-$ represents an anionic counterion.

Hereinafter, the compound expressed by Formula (1) (specific colorant) will be described in detail. In the following, first, the substituent including a partial structure expressed by Formula (1b) specified in Requirement 1 will be described.

Examples of the cationic group of $X_1^+$ in Formula (1b) include groups expressed by Formula (N1) described below, groups expressed by Formula (P1) described below, groups expressed by Formula (CyN1) described below, and groups expressed by Formula (CyN2) described below.

$*—N^+(R^A)_3$ Formula (N1):

$*—P^+(R^B)_3$ Formula (P1):

In Formulas (N1) and (P1), $R^A$ and $R^B$ each independently represent a hydrogen atom or a substituent.

The substituents represented by $R^A$ and $R^B$ are not particularly limited, and examples thereof include alkyl groups and aryl groups.

The alkyl group is preferably linear or branched. The number of carbon atoms in the alkyl group is preferably 1 to 8, more preferably 1 to 6, and still more preferably 1 to 3. The alkyl group may further have a substituent. Examples of the substituent include a hydroxyl group and a cyano group.

The aryl group is preferably a phenyl group. The aryl group may further have a substituent. Examples of the substituent include alkyl groups (preferably having 1 to 6 carbon atoms), a hydroxyl group, and a cyano group.

$R^A$ and $R^B$ are particularly preferably a hydrogen atom or a linear or branched alkyl group having 1 to 3 carbon atoms, and a hydrogen atom is more preferable.

In Formulas (N1) and (P1), * represents a bonding position.

[Chemical Formula 3]

(CyN1)

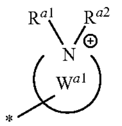

(CyN2)

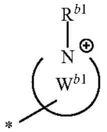

In Formula (CyN1), $R^{a1}$ and $R^{a2}$ each independently represent a hydrogen atom or a substituent. $W^{a1}$ represents an alicyclic ring including at least one cationic nitrogen atom specified in the formula. The alicyclic ring may further have a substituent other than $R^{a1}$ and $R^{a2}$. * represents a bonding position.

In Formula (CyN2), $R^{b1}$ represents a hydrogen atom or a substituent. $W^{b1}$ represents an aromatic ring including at least one cationic nitrogen atom specified in the formula. The aromatic ring may further have a substituent other than $R^{b1}$. * represents a bonding position.

Examples of the substituents represented by $R^{a1}$, $R^{a2}$, and $R^{b1}$ in Formulas (CyN1) and (CyN2) include the same as examples of the substituents represented by $R^A$ and $R^B$ in Formulas (N1) and (P1) described above, and the preferred embodiments of the substituents represented by $R^{a1}$, $R^{a2}$, and $R^{b1}$ are also the same as those of the substituents represented by $R^A$ and $R^B$.

In Formula (CyN1), $W^{a1}$ represents an alicyclic ring including at least one cationic nitrogen atom specified in Formula (CyN1).

The number of ring members in the alicyclic ring is not particularly limited, and is preferably 3 to 10, more preferably 5 to 8, and still more preferably 5 to 6. The alicyclic ring may have a monocyclic structure or a condensed ring structure obtained by a condensation reaction of two or more rings, and a monocyclic structure is particularly preferable.

Examples of the atom (ring member atom) included in the alicyclic ring include the cationic nitrogen atom specified in Formula (CyN1), a carbon atom, and heteroatoms that may be optionally included other than the cationic nitrogen atom specified in Formula (CyN1) (other heteroatoms).

In a case where the alicyclic ring has other heteroatoms as ring member atoms, the number of other heteroatoms is not particularly limited, and is preferably, for example, 1 to 2. Examples of other heteroatoms include a sulfur atom, an oxygen atom, a nitrogen atom, and a phosphorus atom, and a sulfur atom, an oxygen atom, or a nitrogen atom is preferable.

From the viewpoint of obtaining a more excellent effect of one or more embodiments of the present invention, the ring member atoms in the alicyclic ring preferably include only the cationic nitrogen atom specified in Formula (CyN1) and a carbon atom.

The alicyclic ring may further have a substituent other than $R^{a1}$ and $R^{a2}$.

The substituent is not particularly limited, and examples of the substituent include a hydroxyl group, a cyano group, alkyl groups, alkylcarbonyloxy groups (preferably having 2 to 8 carbon atoms), alkylaminocarbonyloxy groups (preferably having 2 to 8 carbon atoms), a cyano group, a carbamoyl group, alkylcarbamoyl groups (preferably having 2 to 8 carbon atoms), arylcarbamoyl groups (preferably having 7 to 11, and more preferably 7 carbon atoms), and aryl groups (preferably a phenyl group).

From the viewpoint of obtaining a more excellent effect of one or more embodiments of the present invention, the alicyclic ring is also preferably an alicyclic ring that has no substituent other than $R^{a1}$ and $R^{a2}$.

The bonding position represented by * is formed by removing one hydrogen atom included in the ring member atoms of the alicyclic ring.

Specific examples of Formula (CyN1) include groups expressed by Formula (CyN1-1) described below.

[Chemical Formula 4]

(CyN1-1)

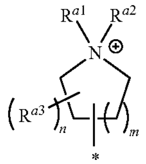

In Formula (CyN1-1), $R^{a1}$ and $R^{a2}$ mean the same as $R^{a1}$ and $R^{a2}$ in Formula (CyN1), respectively, and preferred embodiments thereof are also the same as those in Formula (CyN1).

$R^{a3}$ represents a substituent. Examples of the substituent include the substituents described above as a substituent that the alicyclic ring may have other than $R^{a1}$ and $R^{a2}$.

m represents an integer of 1 to 3, preferably 1 or 2, and more preferably 2.

n represents an integer of 0 to 3, and preferably 0.

* represents a bonding position.

The bonding position represented by * is formed by removing one hydrogen atom included in the ring member atoms of the alicyclic ring.

In Formula (CyN2), $W^{b1}$ represents an aromatic ring including at least one cationic nitrogen atom specified in the formula.

The number of ring members in the aromatic ring is not particularly limited, and is preferably 3 to 10, more preferably 5 to 8, and still more preferably 5 to 6. The aromatic ring may have a monocyclic structure or a condensed ring structure obtained by a condensation reaction of two or more rings, and a monocyclic structure is particularly preferable.

Examples of the heteroatom in the aromatic ring include the cationic nitrogen atom specified in Formula (CyN2), a carbon atom, and heteroatoms that may be optionally included other than the cationic nitrogen atom specified in Formula (CyN2) (other heteroatoms).

In a case where the aromatic ring has other heteroatoms as ring member atoms, the number of other heteroatoms is not particularly limited, and is preferably, for example, 1 to 2. Examples of other heteroatoms include a sulfur atom, an oxygen atom, a nitrogen atom, and a phosphorus atom, and a sulfur atom, an oxygen atom, or a nitrogen atom is preferable.

From the viewpoint of obtaining a more excellent effect of one or more embodiments of the present invention, the ring member atoms in the aromatic ring preferably include only the cationic nitrogen atom specified in Formula (CyN2) and a carbon atom.

The aromatic ring may further have a substituent other than $R^{b1}$.

The substituent is not particularly limited, and examples of the substituent include a hydroxyl group, a cyano group, alkyl groups, alkylcarbonyloxy groups (preferably having 2 to 8 carbon atoms), alkylaminocarbonyloxy groups (preferably having 2 to 8 carbon atoms), a cyano group, a carbamoyl group, alkylcarbamoyl groups (preferably having 2 to 8 carbon atoms), arylcarbamoyl groups (preferably having 7 to 11, and more preferably 7 carbon atoms), and aryl groups (preferably a phenyl group).

From the viewpoint of obtaining a more excellent effect of one or more embodiments of the present invention, the aromatic ring is also preferably an aromatic ring that has no substituent other than $R^{b1}$.

The bonding position represented by * is formed by removing one hydrogen atom included in the ring member atoms of the aromatic ring.

Specific examples of Formula (CyN2) include groups expressed by Formula (CyN2-1) described below.

[Chemical Formula 5]

(CyN2-1)

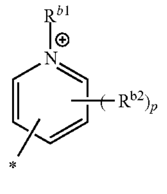

In Formula (CyN2-1), $R^{b1}$ means the same as $R^{b1}$ in Formula (CyN2), and a preferred embodiment thereof is also the same as that in Formula (CyN2).

$R^{b2}$ represents a substituent. Examples of the substituent include the substituents described above as a substituent that the aromatic ring group may have other than $R^{b1}$.

p represents an integer of 0 to 4, preferably an integer of 0 to 2, and more preferably 0.

* represents a bonding position.

The bonding position represented by * is formed by removing one hydrogen atom included in the ring member atoms of the aromatic ring.

In Formula (1b), the anionic counterion of $Y^-$ is not particularly limited, and examples of the anionic counterion include sulfonimide ions, anions of perhalogenated Lewis acids, halide ions, anions of arylsulfonates, and a saccharin ion.

The sulfonimide ions are ions represented by $Rf—SO_2—N^-—SO_2—Rf$. Rf represents a perfluoroalkyl group having 1 to 8 (preferably 1 to 6) carbon atoms.

Examples of the anions of perhalogenated Lewis acids include $PF_6^-$, $SbF_6^-$, $BF_4^-$, $AsF_6^-$, and $FeCl_4^-$.

Examples of the halide ions include $Cl^-$, $Br^-$, and $I^-$.

Examples of the anions of arylsulfonates include $p—CH_3C_6H_4SO_3^-$ and $PhSO_3^-$.

From the viewpoint of obtaining a more excellent effect of one or more embodiments of the present invention, the anionic counterion of $Y^-$ is preferably one or more selected from the group consisting of sulfonimide ions, a hexafluorophosphate ion ($PF_6^-$), an iodide ion ($I^-$), a saccharin ion, and a tosylate ion ($p—CH_3C_6H_4SO_3^-$).

Examples of the substituent including a partial structure expressed by Formula (1b) in Requirement 1 above include substituents expressed by Formula (T1) described below.

$$*—L_{T1}—X_1^+Y^- \qquad \text{Formula (T1):}$$

Formula (T1), $X_1^+$ and $Y^-$ mean the same as $X_1^+$ and $Y^-$ in Formula (1b), respectively, and preferred embodiments thereof are also the same as those in Formula (1b).

$L_{T1}$ represents a single bond or a divalent linking group.

The divalent linking group represented by $L_{T1}$ is not particularly limited, and examples of the divalent linking group include —CO—, —O—, —S—, —SO—, $—SO_2—$, $—NR^X—$, alkylene groups (that may be linear, branched, or cyclic, and preferably have 1 to 15, and more preferably 1 to 6 carbon atoms), alkenylene groups (preferably having 2 to 6 carbon atoms), divalent aliphatic heterocyclic groups (that are preferably a 5 to 10-membered ring, more preferably a 5 to 7-membered ring, and still more preferably a 5 to 6-membered ring having at least one nitrogen atom, oxygen atom, or sulfur atom in the ring structure), divalent arylene groups (that are preferably a 6 to 10-membered ring, and more preferably a 6-membered ring), divalent heteroarylene groups (that are preferably a 5 to 10-membered ring, more preferably a 5 to 7-membered ring, and still more preferably a 5 to 6-membered ring having at least one nitrogen atom, oxygen atom, or sulfur atom in the ring structure), and divalent linking groups obtained by combining a plurality of groups in these groups.

Examples of $R^X$ include a hydrogen atom and monovalent organic groups. The monovalent organic group is not particularly limited, and is preferably, for example, an alkyl group (preferably having 1 to 6 carbon atoms).

The alkylene groups, the alkenylene groups, the divalent aliphatic heterocyclic groups, the divalent arylene groups, and the divalent heteroarylene groups may have a substituent.

$L_{T1}$ is particularly preferably a single bond.

Next, Formula (1) will be described in detail.

In Formula (1), the substituents represented by $R^1$ and $R^2$ are not particularly limited, and examples thereof include substituents including a partial structure expressed by Formula (1b) described above, and alkyl groups.

The alkyl groups represented by $R^1$ and $R^2$ may be linear, branched, or cyclic.

The number of carbon atoms in the linear or branched alkyl group represented by each of $R^1$ and $R^2$ is, for example, preferably 1 to 12, more preferably 1 to 8, and still more preferably 1 to 5.

The cyclic alkyl group represented by each of $R^1$ and $R^2$ may be a monocyclic ring or a polycyclic ring. The number of carbon atoms is preferably 5 to 12, more preferably 5 or 6, and still more preferably 6.

The alkyl groups represented by $R^1$ and $R^2$ may further have a substituent. Examples of the substituent include a hydroxyl group, a cyano group, a carbamoyl group, aryl groups (aryl groups preferably having 6 to 10 carbon atoms, and more preferably a phenyl group), and substituents including a partial structure expressed by Formula (1b) described above.

Examples of the alkyl groups represented by $R^1$ and $R^2$ include linear or branched alkyl groups such as $—CH_3$, $—C_2H_5$, $—CH_2)_2CH_3$, $—CH(CH_3)_2$, $—(CH_2)_3CH_3$, $—CH_2CH(CH_3)_2$, $—CH(CH_3)CH_2CH_3$, $—C\ (CH_3)_3$, $—(CH_2)_4CH_3$, $—(CH_2)_2CH(CH_3)_2$, $—(CH_2)_5CH_3$, $—(CH_2)_7CH_3$, $—(CH_2)_9CH_3$, $—(CH_2)_{11}CH_3$, $—CH_2OCOCH_3$, $—CH_2OCOCH(CH_3)_2$, $—CH_2OCOCH(C_2H_5)CH_2CH_2CH_2CH_3$, $—CH_2OCONHCH(CH_3)_2$, $—CH_2OH$, $—CH_2CN$, $—CH_2CONH_2$, $—CH_2CONHPh$, and $—CH_2Ph$ (Ph represents a phenyl group).

$R^1$ and $R^2$ are optionally bonded to each other to form a ring.

The ring formed by bonding $R^1$ and $R^2$ to each other is not particularly limited, and may be an alicyclic ring or an aromatic ring, but is preferably an alicyclic ring.

The ring formed by bonding $R^1$ and $R^2$ to each other may have a monocyclic structure or a condensed ring structure obtained by a condensation reaction of two or more rings, and a monocyclic structure is particularly preferable.

The ring formed by bonding $R^1$ and $R^2$ to each other preferably includes a partial structure of $X_2^+(Y^-)$. Here, $X_2^+$ represents a cationic atom constituting a ring member atom of the ring, and $Y^-$ represents an anionic counterion.

Examples of the cationic atom represented by $X_2^+$ include a cationic nitrogen atom ($N^+$) and a cationic phosphorus atom ($P^+$), and a cationic nitrogen atom ($N^+$) is preferable.

In the ring formed by bonding $R^1$ and $R^2$ to each other, a cationic nitrogen atom ($N^+$) is preferably in the form of $*—N^+(R^C)\ (R^D)—*$ or $*—N^+(R^E)=*$, and a cationic phosphorus atom ($P^+$) is preferably in the form of $*—P^+(R^E)_2—*$ or $*—P^+(RG)=*$. $R^C$, $R^D$, $R^E$, $R^E$, and $R^G$ each independently represent a hydrogen atom or a substituent. Examples of the substituents represented by $R^C$, $R^D$, $R^E$, $R^E$, and $R^G$ include the same as examples of the substituents represented by $R^A$ and $R^B$ in Formulas (N1) and (P1) described above. * represents a bonding position. In $*—P^+(R^F)_2—*$, the two $R^F$s may be the same or different.

Examples of the anionic counterion represented by $Y^-$ include the same as examples of the anionic counterion represented by $Y^-$ of the substituent including a partial structure expressed by Formula (1b) described above.

The number of ring members in the ring formed by bonding $R^1$ and $R^2$ to each other is not particularly limited, and is preferably 3 to 10, more preferably 5 to 8, and still more preferably 5 to 6.

In a case where the ring formed by bonding $R^1$ and $R^2$ to each other includes a partial structure of $X_2^+\ (Y^-)$, at least one of the ring member atoms corresponds to the cationic atom represented by $X_2^+$ described above.

In a case where the ring formed by bonding $R^1$ and $R^2$ to each other includes a partial structure of $X_2^+\ (Y^-)$, examples of the ring member atom of the ring include the above-described cationic atoms represented by $X_2^+$, a carbon atom, and heteroatoms that may be optionally included other than the above-described cationic atoms represented by $X_2^+$ (other heteroatoms).

In a case where the ring formed by bonding $R^1$ and $R^2$ to each other has other heteroatoms as ring member atoms, the number of other heteroatoms is not particularly limited, and is preferably, for example, 1 to 2. Examples of other heteroatoms include a sulfur atom, an oxygen atom, a nitrogen atom, and a phosphorus atom, and a sulfur atom, an oxygen atom, or a nitrogen atom is preferable.

The ring formed by bonding $R^1$ and $R^2$ to each other may further have a substituent other than the substituents (for example, $R^C$, $R^D$, $R^E$, $R^F$, and $R^G$ as above) that may be included in the cationic atom.

The substituent is not particularly limited, and examples of the substituent include a hydroxyl group, a cyano group, alkyl groups, alkylcarbonyloxy groups (preferably having 2 to 8 carbon atoms), alkylaminocarbonyloxy groups (preferably having 2 to 8 carbon atoms), a cyano group, a carbamoyl group, alkylcarbamoyl groups (preferably having 2 to 8 carbon atoms), arylcarbamoyl groups (preferably having 7 to 11, and more preferably 7 carbon atoms), and aryl groups (preferably a phenyl group).

The ring member atoms of the ring formed by bonding $R^1$ and $R^2$ to each other are not particularly limited in a case where the ring does not include a partial structure of $X_2^+$ ($Y^-$), and the ring member atoms may include, for example, only a carbon atom, or a carbon atom and a heteroatom. Examples of the heteroatom include a sulfur atom, an oxygen atom, a nitrogen atom, and a phosphorus atom, and a sulfur atom, an oxygen atom, or a nitrogen atom is preferable. The number of heteroatoms in the ring is not particularly limited, and is preferably, for example, 1 to 2.

The ring may further have a substituent. The substituent is not particularly limited, and examples of the substituent include a hydroxyl group, a cyano group, alkyl groups, alkylcarbonyloxy groups (preferably having 2 to 8 carbon atoms), alkylaminocarbonyloxy groups (preferably having 2 to 8 carbon atoms), a cyano group, a carbamoyl group, alkylcarbamoyl groups (preferably having 2 to 8 carbon atoms), arylcarbamoyl groups (preferably having 7 to 11, and more preferably 7 carbon atoms), and aryl groups (preferably a phenyl group).

In a case where $R^1$ and $R^2$ are bonded to each other to form a ring, the compound expressed by Formula (1) is preferably a compound expressed by Formula (1A) described below from the viewpoint of obtaining a more excellent effect of one or more embodiments of the present invention.

[Chemical Formula 6]

(1A)

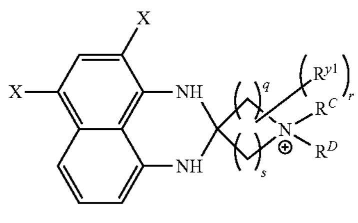

In Formula (1A), X means the same as X in Formula (1).

$R^C$ and $R^D$ each independently represent a hydrogen atom or a substituent. Examples of the substituents represented by $R^C$ and $R^D$ include the same as examples of the substituents represented by $R^A$ and $R^B$ in Formulas (N1) and (P1) described above.

$R^{y1}$ represents a substituent. The substituent means the same as $R^{a3}$ in Formula (CyN1-1), and a preferred embodiment thereof is also the same as that in Formula (CyN1-1).

q represents an integer of 1 to 3, preferably 1 or 2, and more preferably 2.

s represents an integer of 1 to 3, preferably 1 or 2, and more preferably 2.

r represents an integer of 0 to 3, and preferably 0.

In Formula (1), one of two Xs represents a hydrogen atom, and the other represents a group expressed by Formula (1a) described above.

Hereinafter, the group expressed by Formula (1a) will be described in detail.

Examples of the substituents represented by $R^3$ to $R^7$ in Formula (1a) include substituents including a partial structure expressed by Formula (1b) described above, halogen atoms, —CN, —CO—O—$R_{X1}$, —O—CO—$R_{X2}$, —CO—$R_{X3}$, and —$NO_2$.

$R_{X1}$ and $R_{X2}$ each independently represent an alkyl group. $R_{X3}$ represents an alkyl group or an aryl group.

The alkyl groups represented by $R_{X1}$, $R_{X2}$, and $R_{X3}$ may be linear, branched, or cyclic, and are preferably linear or branched.

The number of carbon atoms in the alkyl group represented by each of $R_{X1}$, $R_{X2}$, and $R_{X3}$ is preferably 1 to 11, more preferably 1 to 7, and still more preferably 1 to 4.

The aryl group represented by $R_{X3}$ is preferably an aryl group having 6 to 11 carbon atoms, and more preferably a phenyl group.

Examples of the halogen atoms represented by $R^3$ to $R^7$ include a fluorine atom, a chlorine atom, a bromine atom, and an iodine atom, and a fluorine atom or a chlorine atom is preferable, and a chlorine atom is more preferable.

As the substituents represented by $R^3$ to $R^7$, a substituent including a partial structure expressed by Formula (1b) described above, a fluorine atom, a chlorine atom, —CN, —$NO_2$, —CO—O—$R_{X1}$ ($R_{X1}$ is an alkyl group having 1 to 11 carbon atoms), or —CO—$R_{X3}$ ($R_{X3}$ is an alkyl group having 1 to 11 carbon atoms or an aryl group having 6 to 11 carbon atoms) is preferable, a chlorine atom, —CN, —$NO_2$, —CO—O—$R_{X1}$ ($R_{X1}$ is an alkyl group having 1 to 4 carbon atoms), or —CO—$R_{X3}$ ($R_{X3}$ is an alkyl group having 1 to 4 carbon atoms) is more preferable, and a chlorine atom is still more preferable.

From the viewpoint of obtaining a more excellent effect of one or more embodiments of the present invention, in Formula (1a), at least one of $R^3$ to $R^7$ preferably represents a substituent, and it is particularly more preferable that $R^3$ represent a substituent and $R^4$ to $R^7$ represent a hydrogen atom.

In Formula (1a), the substituents represented by $R^8$ to $R^{13}$ are not particularly limited, and examples thereof include substituents including a partial structure expressed by Formula (1b) described above, a hydroxyl group, a cyano group, alkyl groups, alkylcarbonyloxy groups (preferably having 2 to 8 carbon atoms), alkylaminocarbonyloxy groups (preferably having 2 to 8 carbon atoms), a cyano group, a carbamoyl group, alkylcarbamoyl groups (preferably having 2 to 8 carbon atoms), arylcarbamoyl groups (preferably having 7 to 11, and more preferably 7 carbon atoms), and aryl groups (preferably a phenyl group).

From the viewpoint of obtaining a more excellent effect of one or more embodiments of the present invention, $R^8$ to $R^{13}$ in Formula (1a) preferably represent a hydrogen atom.

In Formula (1a), two adjacent groups among $R^3$ to $R^{13}$ are optionally bonded to each other to form a ring.

The ring formed by bonding two adjacent groups among $R^3$ to $R^{13}$ to each other is not particularly limited, and may be an alicyclic ring or an aromatic ring.

The ring formed by bonding two adjacent groups among $R^3$ to $R^{13}$ to each other may have a monocyclic structure or a condensed ring structure obtained by a condensation reaction of two or more rings.

The ring formed by bonding two adjacent groups among $R^3$ to $R^{13}$ to each other preferably includes a partial structure of $X_3^+$ ($Y^-$). Here, $X_3^+$ represents a cationic atom constituting a ring member atom of the ring, and $Y^-$ represents an anionic counterion.

Examples of the cationic atom represented by $X_3^+$ include a cationic nitrogen atom ($N^+$) and a cationic phosphorus atom ($P^+$), and a cationic nitrogen atom ($N^+$) is preferable.

In the ring formed by bonding two adjacent groups among $R^3$ to $R^{13}$ to each other, a cationic nitrogen atom ($N^+$) is preferably in the form of *—$N^+$ ($R^H$) ($R^I$)—* or *—$N^+$ ($R^J$)=*, and a cationic phosphorus atom ($P^+$) is preferably in the form of *—$P^+$ $(R^K)_2$—* or *—$P^+$ ($R^L$)=*. $R^H$, $R^I$, $R^J$, $R^K$, and $R^L$ described above each independently represent a hydrogen atom or a substituent. Examples of the substituents represented by the $R^H$, $R^I$, $R^J$, $R^K$, and $R^L$ include the same as examples of the substituents represented by $R^A$ and $R^B$ in Formulas (N1) and (P1) described above. * represents a bonding position. In *—$P^+$ $(R^K)_2$—*, the two $R^K$s may be the same or different.

Examples of the anionic counterion represented by $Y^-$ include the same as examples of the anionic counterion represented by $Y^-$ of the substituent including a partial structure expressed by Formula (1b) described above.

The number of ring members in the ring formed by bonding two adjacent groups among $R^3$ to $R^{13}$ to each other is not particularly limited, and is preferably 3 to 10, more preferably 5 to 8, and still more preferably 5 to 6.

In a case where the ring formed by bonding two adjacent groups among $R^3$ to $R^{13}$ to each other includes a partial structure of $X_3^+$ ($Y^-$), at least one of the ring member atoms corresponds to the cationic atom represented by $X_3^+$ described above.

In a case where the ring formed by bonding two adjacent groups among $R^3$ to $R^{13}$ to each other includes a partial structure of $X_3^+$ ($Y^-$), examples of the ring member atom of the ring include the above-described cationic atoms represented by $X_3^+$, a carbon atom, and heteroatoms that may be optionally included other than the above-described cationic atoms represented by $X_3^+$ (other heteroatoms).

In a case where the ring formed by bonding two adjacent groups among $R^3$ to $R^{13}$ to each other has other heteroatoms as ring member atoms, the number of other heteroatoms is not particularly limited, and is preferably, for example, 1 to 2. Examples of other heteroatoms include a sulfur atom, an oxygen atom, a nitrogen atom, and a phosphorus atom, and a sulfur atom, an oxygen atom, or a nitrogen atom is preferable.

The ring formed by bonding two adjacent groups among $R^3$ to $R^{13}$ to each other may further have a substituent other than the substituents (for example, $R^H$, $R^I$, $R^J$, $R^K$, and $R^L$ described above) that may be included in the cationic atom.

The substituent is not particularly limited, and examples of the substituent include a hydroxyl group, a cyano group, alkyl groups, alkylcarbonyloxy groups (preferably having 2 to 8 carbon atoms), alkylaminocarbonyloxy groups (preferably having 2 to 8 carbon atoms), a cyano group, a carbamoyl group, alkylcarbamoyl groups (preferably having 2 to 8 carbon atoms), arylcarbamoyl groups (preferably having 7 to 11, and more preferably 7 carbon atoms), and aryl groups (preferably a phenyl group).

The ring member atoms of the ring formed by bonding two adjacent groups among $R^3$ to $R^{13}$ to each other are not particularly limited in a case where the ring does not include a partial structure of $X_3^+$ ($Y^-$), and the ring member atoms may include, for example, only a carbon atom, or a carbon atom and a heteroatom. Examples of the heteroatom include a sulfur atom, an oxygen atom, a nitrogen atom, and a phosphorus atom, and a sulfur atom, an oxygen atom, or a nitrogen atom is preferable. The number of heteroatoms in the ring is not particularly limited, and is preferably, for example, 1 to 2.

The ring may further have a substituent. The substituent is not particularly limited, and examples of the substituent include a hydroxyl group, a cyano group, alkyl groups, alkylcarbonyloxy groups (preferably having 2 to 8 carbon atoms), alkylaminocarbonyloxy groups (preferably having 2 to 8 carbon atoms), a cyano group, a carbamoyl group, alkylcarbamoyl groups (preferably having 2 to 8 carbon atoms), arylcarbamoyl groups (preferably having 7 to 11, and more preferably 7 carbon atoms), and aryl groups (preferably a phenyl group).

Examples of the ring formed by bonding two adjacent groups among $R^3$ to $R^{13}$ to each other include a pyridinium ring.

The specific colorant satisfies at least one of Requirements 1 to 3 described above. From the viewpoint of obtaining a more excellent effect of one or more embodiments of the present invention, in Formula (1), at least one of $R^1$ or $R^2$ preferably represents a substituent including a partial structure expressed by Formula (1b) described above, or $R^1$ and $R^2$ are preferably bonded to each other to form a ring including a partial structure of $X_2^+$ ($Y^-$) described above. In other words, it is preferable that the specific colorant satisfy Requirement 1 and at least one of $R^1$ or $R^2$ represent a substituent including a partial structure expressed by Formula (1b) described above, or that the specific colorant satisfy Requirement 2.

From the viewpoint of obtaining a more excellent effect of one or more embodiments of the present invention, in the compound of one or more embodiments of the present invention, it is preferable that in the two Xs specified in Formula (1), X at the para-position with respect to NH specified in Formula (1) represent a group expressed by Formula (1a) and that X at the ortho-position with respect to NH specified in Formula (1) represent a hydrogen atom.

Hereinafter, a specific example of the specific colorant will be shown, but the specific colorant is not limited thereto.

[Chemical Formula 7]

Compound 1

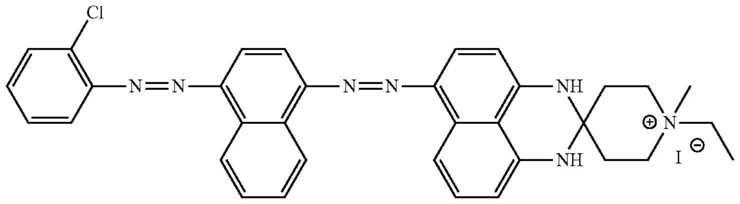

Compound 2

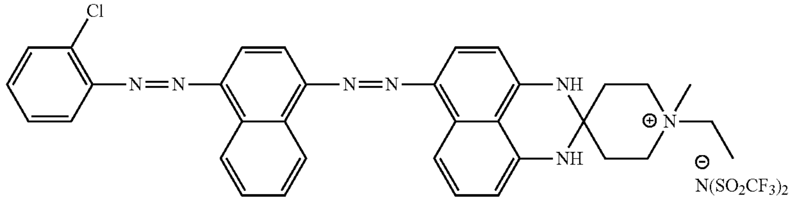

Compound 3

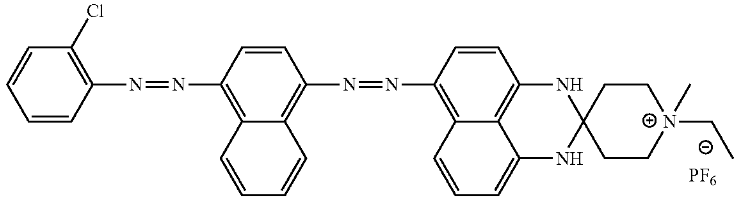

Compound 4

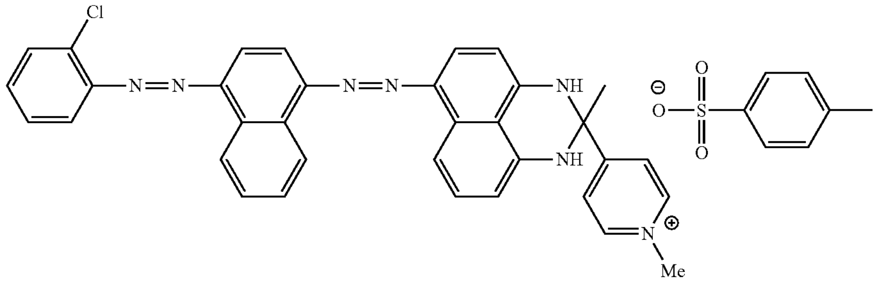

-continued

Compound 5

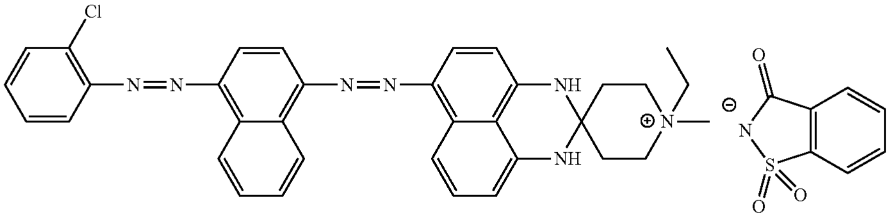

Compound 6

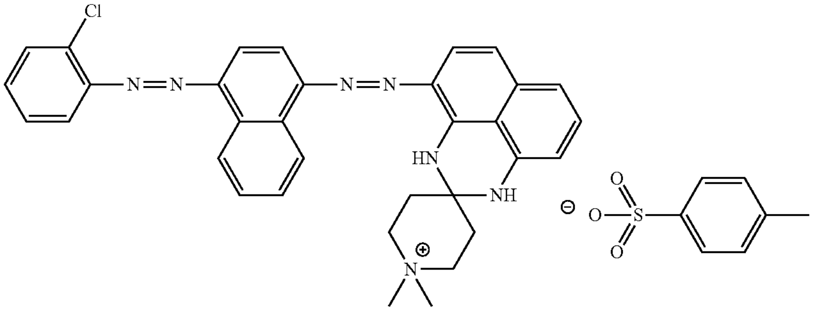

The specific colorant can be synthesized in accordance with a known method. Examples of the method for synthesizing the specific colorant include the following method including Steps 1 to 4 in according with the method described in WO 2020/067063 A. As the reagents and the solvents used in Steps 1 to 4, the same reagents and solvents as those described in WO 2020/067063 A can be used.

Step 1: a step of obtaining a condensate by a condensation reaction between 1, 8-diaminonaphthalene and a ketone compound.

Step 2: a step of converting o-substituted aniline into a diazonium salt using a diazotizing agent, and then coupling the diazonium salt with 1-naphthylamine to obtain a monoazo compound.

Step 3: a step of converting the monoazo compound obtained in Step 2 into a diazonium salt using a diazotizing agent, and then coupling the diazonium salt with the condensate obtained in Step 1 to obtain a disazo compound.

Step 4: a step of adding the disazo compound obtained in Step 3 into a solution (for example, acetone solution) containing a salt (for example, an alkali metal salt or an organic salt) capable of releasing one anionic ion selected from the group consisting of, for example, sulfonimide ions, a hexafluorophosphate ion, an iodide ion, a saccharin ion, and a tosylate ion, and introducing a site of an ion pair into the disazo compound to obtain a specific colorant.

Step 4 may be a step of adding the disazo compound obtained in Step 3 into a solution containing a salt capable of releasing an anionic ion, introducing a site of an ion pair into the disazo compound, and then converting the counter anion species in the compound obtained by the above procedure into another counter anion species by salt exchange to obtain a specific colorant.

The content of the specific colorant in the colored fiber is preferably 0.001 to 10 parts by mass, more preferably 0.01 to 5 parts by mass, and still more preferably 0.05 to 3 parts by mass with respect to 100 parts by mass of the fiber.

Fiber

The colored fiber of one or more embodiments of the present invention includes a fiber.

The fiber is not particularly limited, and is preferably a synthetic fiber, and more preferably an acrylic fiber including an acrylic polymer.

Examples of the acrylic polymer include homopolymers of a repeating unit derived from an acrylonitrile monomer and copolymers including a repeating unit derived from an acrylonitrile monomer. The copolymer including a repeating unit derived from an acrylonitrile monomer may be a block copolymer, a random copolymer, or an alternating copolymer.

The acrylic polymer is particularly preferably a copolymer including a repeating unit derived from an acrylonitrile monomer.

The acrylic polymer is preferably a polymer including a repeating unit derived from an acrylonitrile monomer and a repeating unit derived from another monomer different from the acrylonitrile monomer, and having a content of the repeating unit derived from the acrylonitrile monomer of less than 95 mass& with respect to the total mass of the acrylic polymer. From the viewpoint of more excellent suitability as an acrylic fiber for artificial hair, the acrylic polymer more preferably has a content of the repeating unit derived from the acrylonitrile monomer of less than 80 mass % with respect to the total mass of the acrylic polymer. The lower limit is not particularly limited, and is, for example, 20 mass % or more.

Examples of the repeating unit derived from another monomer different from the acrylonitrile monomer include repeating units derived from a halogen-containing vinylidene monomer and repeating units derived from a halogen-containing vinyl monomer. Examples of the repeating unit derived from another vinyl-based monomer different from the acrylonitrile monomer, the halogen-containing vinylidene monomer, and the halogen-containing vinyl monomer include repeating units derived from a sulfonate group-containing vinyl monomer.

Examples of a specific aspect of the acrylic polymer include an aspect in which the acrylic polymer includes a repeating unit X derived from an acrylonitrile monomer, one or more kinds of repeating units Y selected from the group consisting of repeating units derived from a halogen-containing vinylidene monomer and repeating units derived from a halogen-containing vinyl monomer, and a repeating unit Z derived from another vinyl-based monomer different from the acrylonitrile monomer, the halogen-containing vinylidene monomer, and the halogen-containing vinyl monomer, the content of the repeating unit X is 29.5 to 79.5 mass % (preferably 34.5 to 74.5 mass %) with respect to the total mass of the acrylic polymer, the content of the repeating units Y is 20 to 70 mass % (preferably 25 to 65 mass %) with respect to the total mass of the acrylic polymer, and the content of the repeating unit Z is 0.5 to 5 mass % (preferably 0.6 to 3 mass %) with respect to the total mass of the acrylic polymer.

If the content of the repeating unit X is in the above numerical range, an effect of one or more embodiments of the present invention is more excellent. If the content of the repeating units Y is in the above numerical range, the flame retardancy is more excellent. If the repeating unit derived from another vinyl monomer is a repeating unit derived from a sulfonate group-containing vinyl monomer described below, the hydrophilicity is more excellent.

The halogen atoms in the halogen-containing vinyl monomer and the halogen-containing vinylidene monomer are particularly preferably a chlorine atom. In other words, the halogen-containing vinyl monomer and the halogen-containing vinylidene monomer are preferably a chlorine atom-containing vinyl monomer and a chlorine atom-containing vinylidene monomer.

Another vinyl-based monomer is preferably a sulfonate group-containing vinyl monomer.

The sulfonate group-containing vinyl monomer is not particularly limited as long as it is a vinyl monomer having one or more sulfonate groups, and examples of the sulfonate group-containing vinyl monomer include allylsulfonic acid, methallylsulfonic acid, styrenesulfonic acid, isoprenesulfonic acid, 2-acrylamide-2-methylpropanesulfonic acid, and metal salts (for example, alkali metal salts) and amine salts thereof. The acrylic polymer may include only one kind, or two or more kinds of repeating units derived from a sulfonate group-containing vinyl monomer.

From the viewpoint of obtaining a more excellent effect of one or more embodiments of the present invention, the acrylic polymer particularly preferably includes a repeating unit X derived from an acrylonitrile monomer, one or more kinds of repeating units Y selected from the group consisting of repeating units derived from a vinylidene chloride monomer and repeating units derived from a vinyl chloride monomer, and a repeating unit Z derived from a sulfonate group-containing vinyl monomer, and it is particularly preferable that the content of the repeating unit X be 29.5 to 79.5 mass % (preferably 34.5 to 74.5 mass %) with respect to the total mass of the acrylic polymer, the content of the repeating units Y be 20 to 70 mass % (preferably 25 to 65 mass %) with respect to the total mass of the acrylic polymer, and the content of the repeating unit Z be 0.5 to 5 mass % (preferably 0.6 to 3 mass %) with respect to the total mass of the acrylic polymer.

The acrylic fiber may further include another polymer other than the acrylic polymer. Examples of another polymer include homopolymers of a repeating unit selected from the group consisting of repeating units derived from a halogen-containing vinylidene monomer and repeating units derived from a halogen-containing vinyl monomer described above.

Fiber Treatment Agent

The colored fiber preferably contains a fiber treatment agent from the viewpoint of more excellent texture.

Examples of a usable fiber treatment agent include anionic surfactants such as phosphate ester salts and sulfate ester salts, cationic surfactants such as quaternary ammonium salts and imidazolium salts, nonionic surfactants such as ethylene oxide and/or propylene oxide adducts and polyhydric alcohol partial esters of fats and oils, animal and vegetable fats and oils, mineral oils, fatty acid esters, and known oil agents such as silicone-based surfactants such as amino-modified silicone.

The fiber treatment agents may be used singly or in combination of two or more kinds thereof.

Another Additive

The colored fiber may include another additive for improvement of a fiber property as necessary. Examples of the additive include titanium dioxide, silicon dioxide, gloss adjusting agents such as esters and ethers of cellulose derivatives including cellulose acetate, colorants such as organic pigments, inorganic pigments, and dyes, stabilizers for improvements of light resistance and heat resistance, fiber sizing agents such as urethane-based polymers and cationic ester polymers for improvements of processability during blade or twist processing, inorganic or organic deodorants capable of capturing isovaleric acid as an odor component generated from scalp, and functional agents such as fragrances capable of imparting fragrance of citrus or the like to artificial hair fibers.

From the viewpoint of improving the blackness of the hue of the colored fiber, the specific colorant is preferably used in combination with a red dye.

Method for Manufacturing Colored Fiber

Method 1 for Manufacturing Colored Fiber

The colored fiber can be manufactured by a manufacturing method including a step of wet-spinning a spinning dope containing a polymer (for example, the above-described acrylic polymer) included in the fiber and the specific colorant. The spinning dope preferably contains a polymer (for example, the above-described acrylic polymer) included in the fiber, the specific colorant, and a solvent.

The solvent is not particularly limited, and a good solvent of the polymer (for example, the above-described acrylic polymer) included in the fiber can be appropriately used. Examples of the solvent include organic solvents such as dimethyl sulfoxide (DMSO), dimethylacetamide (DMAc), N,N-dimethylformamide (DMF), and acetone.

The spinning dope may contain water. In particular, in the case of using dimethyl sulfoxide as the organic solvent, formation of voids can be further suppressed. In a case where a small amount of water is contained, the content of water is, for example, 1.5 to 4.8 mass %.

The spinning dope preferably contains an epoxy group-containing compound. In a case where the spinning dope contains an epoxy group-containing compound, odor, fiber coloring due to heat, fiber devitrification due to hot water, and the like can be suppressed. In particular, in the case of using dimethyl sulfoxide as the organic solvent, generation of a malodorous component due to decomposition of dimethyl sulfoxide can be more effectively suppressed at the time of heating the colored fiber.

The content of the epoxy group-containing compound in the spinning dope is preferably 0.1 parts by mass or more, more preferably 0.2 parts by mass or more, and still more preferably 0.3 parts by mass or more with respect to 100 parts by mass of the polymer (for example, the above-described acrylic polymer) included in the fiber. The upper limit of the content of the epoxy group-containing compound is preferably 5 parts by mass or less, more preferably 3 parts by mass or less, and still more preferably 1 part by mass or less with respect to 100 parts by mass of the polymer (for example, the above-described acrylic polymer) contained in the fiber from the viewpoint of obtaining more excellent spinnability and fiber quality, and better cost.

Examples of a usable epoxy group-containing compound include glycidyl methacrylate-containing polymers, glycidyl acrylate-containing polymers, epoxidized vegetable oils, glycidyl ether epoxy resins, glycidyl amine epoxy resins, glycidyl ester epoxy resins, and cyclic aliphatic epoxy resins.

In the spinning dope, the epoxy group-containing compounds may be used singly or in combination of two or more kinds thereof.

The epoxy group-containing compound is preferably one or more selected from the group consisting of glycidyl methacrylate-containing polymers and glycidyl acrylate-containing polymers, and is more preferably polyglycidyl methacrylate from the viewpoint of obtaining the more excellent epoxy equivalent (mass of the resin containing 1 equivalent of epoxy group), suppression of fiber coloring, solubility in an organic solvent, and reduction in elution into a spinning bath.

The weight average molecular weight of the epoxy group-containing compound is not particularly limited, and can be appropriately determined in consideration of, for example, solubility in an organic solvent and elution into a spinning bath. In a case where the epoxy group-containing compound is one or more selected from the group consisting of glycidyl methacrylate-containing polymers and glycidyl acrylate-containing polymers, for example, the weight average molecular weight is preferably 3,000 or more from the viewpoint of obtaining more excellent reduction in elution into a spinning bath, and the weight average molecular weight is preferably 100,000 or less from the viewpoint of obtaining more excellent solubility into an organic solvent.

The spinning dope may contain another additive for improvement of a fiber property as necessary.

Examples of the additive include titanium dioxide, silicon dioxide, gloss adjusting agents such as esters and ethers of cellulose derivatives including cellulose acetate, colorants such as organic pigments, inorganic pigments, and dyes, and stabilizers for improvement of light resistance and heat resistance.

The step of wet-spinning a spinning dope preferably includes at least a coagulation step, a water washing step, and a drying step.

The step of wet-spinning a spinning dope preferably further includes an in-bath drawing step before the water washing step, or after the water washing step and before the drying step.

The step of wet-spinning a spinning dope preferably further includes an oil agent applying step before the drying step.

The step of wet-spinning a spinning dope preferably further includes a drawing step and a heat relaxation treatment step after the drying step.

First, in the coagulating step, a spinning dope is discharged to a coagulation bath through a spinning nozzle and coagulated to form a yarn (also referred to as coagulated filaments). The cross-sectional shape and the cross-sectional size of the spinning nozzle, the spinning rate, and the spinning conditions such as nozzle draft are appropriately adjusted, and thus a colored fiber having a predetermined cross-sectional shape and cross-sectional size can be obtained.

In the coagulation bath, for example, use can be made of an aqueous solution that has a concentration of a good solvent such as acetone of 25 to 70 mass %. The temperature of the coagulation bath is preferably 5 to 40° C. If the concentration of the organic solvent in the coagulation bath is too low, coagulation is accelerated to roughen the coagulation structure, and thus voids tend to be formed inside the fiber.

Next, in the in-bath drawing step, the colored fiber (coagulated filaments) is preferably subjected to in-bath drawing (also referred to as primary drawing) in a drawing bath. In the drawing bath, use can be made of an aqueous solution which has a lower concentration of a good solvent such as acetone than that in the coagulation bath. The temperature of the drawing bath is preferably 30° C. or higher, more preferably 40° C. or higher, and still more preferably 50° C. or higher. The draw ratio is not particularly limited, and is preferably 2 to 8 from the viewpoint of enhancing the strength and the productivity of the fiber. In the case of performing primary drawing using a water bath, the in-bath drawing step may be performed after the water washing step described below, or primary drawing and water washing may be performed simultaneously.

Next, in the water washing step, the colored fiber is washed with hot water of 30° C. or higher to remove the good solvent such as acetone from the colored fiber. Alternatively, the coagulated filaments may be guided from the coagulation bath to hot water of 30° C. or higher and subjected to the in-bath drawing step and the water washing step simultaneously. In the water washing step, for example, use of hot water of 70° C. or higher facilitates removal of the good solvent such as acetone in the colored fiber.

In the oil agent applying step, an oil agent liquid is used in which a fiber treatment agent is dissolved or dispersed in water. It is preferable that a fiber treatment agent having a predetermined concentration be introduced into an oil agent bath and the yarn having undergone the water washing step be immersed in the fiber treatment agent to apply the fiber treatment agent to the colored fiber.

The temperature of the oil agent bath is not particularly limited, and is, for example, 40° C. or higher, and preferably 40 to 80° C. The immersion time is not particularly limited, and is, for example, 1 to 10 seconds, and preferably 1 to 5 seconds.

The oil agent liquid may contain another additive for improvement of a fiber property as necessary.

Next, in the drying step, the colored fiber to which the fiber treatment agent has been applied is dried. The drying temperature is not particularly limited, and is, for example, 110 to 190° C.

The dried fiber may then be further subjected to drawing (secondary drawing) as necessary. The drawing temperature in the secondary drawing is not particularly limited, and is, for example, 110 to 190° C. The draw ratio is not particularly limited, and is preferably, for example, 1 to 4. The total draw ratio of drawing including the in-bath drawing before drying is preferably 2 to 12.

The fiber obtained by drying or drying and then additional drawing is preferably further relaxed in the heat relaxation treatment step. The relaxation ratio is not particularly limited, and is, for example, preferably 5% or more, and more preferably 10 to 30%. The heat relaxation treatment is preferably performed at a high temperature, and can be performed, for example, in a dry heat atmosphere or a superheated steam atmosphere at 150 to 200° C.

The single fiber fineness of the colored fiber is preferably 10 to 100 dtex, and more preferably 20 to 95 dtex from the viewpoint of preferred use of the colored fiber as artificial hair.

Method 2 for Manufacturing Colored Fiber

The colored fiber can also be manufactured by a manufacturing method including a step of dyeing a fiber using an aqueous solution containing a specific colorant.

The concentration of the specific colorant is not particularly limited, and is, for example, 5.0 mass % or less, and preferably 0.05 to 3.0 mass % with respect to the total mass of the fiber.

The temperature of the aqueous solution is not particularly limited, and is, for example, 50 to 100° C., and preferably 70 to 100° C. The immersion time is not particularly limited, and is, for example, 180 minutes or less, and preferably 10 to 120 minutes.

After the dyeing step, a drying step is preferably performed.

The drying temperature is not particularly limited, and is, for example, 30 to 200° C., and preferably 50 to 180° C.

The dried fiber may then be further subjected to drawing (secondary drawing) as necessary.

The single fiber fineness of the colored fiber is preferably 10 to 100 dtex, and more preferably 20 to 95 dtex from the viewpoint of preferred use of the colored fiber as artificial hair.

Application of Colored Fiber

The application of the colored fiber is not particularly limited, and the colored fiber can be used in various fiber products.

Examples of the fiber products include head decoration products such as fiber bundles for hair, weaving products, wigs, braids, toupees, hair extensions, and hair accessories.

In the case of applying the colored fiber to a head decoration product, another fiber for artificial hair may be included in addition to the colored fiber. Another fiber for artificial hair is not particularly limited, and examples of another fiber include polyvinyl chloride-based fibers, nylon fibers, polyester fibers, and regenerated collagen fibers.

EXAMPLES

Hereinafter, one or more embodiments of the present invention will be described in more detail with reference to Examples. The materials, the used amounts, the proportions, the processing contents, the processing procedures, and the like shown in Examples below can be appropriately changed without departing from the gist of the present disclosure. Therefore, the scope of the present disclosure should not be restrictively interpreted by Examples described below.

Synthesis Example of Specific Colorant: Synthesis of Cationic Dye 1 and Cationic Dye 2

A cationic dye 1 and a cationic dye 2 were synthesized in accordance with the following procedure.

[Chemical Formula 8]

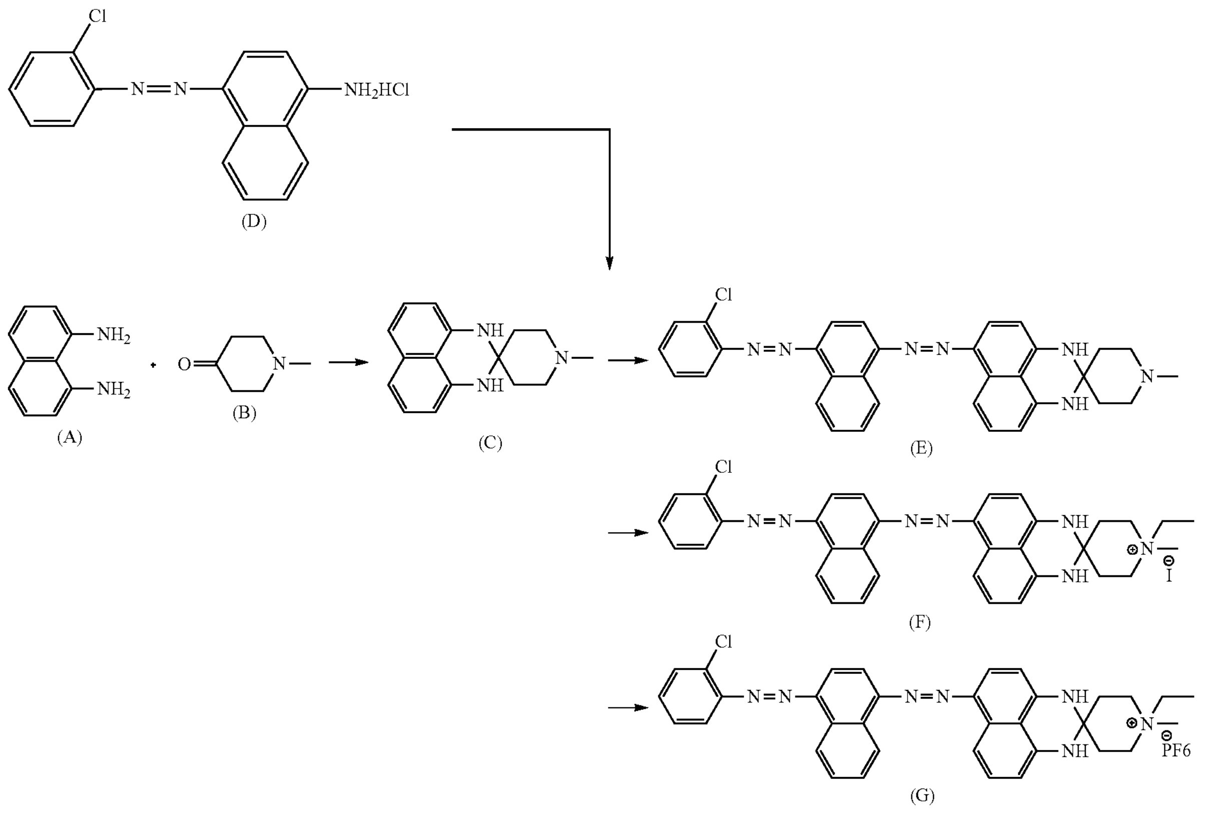

(D) (A) (B) (C) (E) (F) (G)

Synthesis of Intermediate (C)

Into a 2 L three-necked flask, 79.1 g (500 mmol) of 1,8-naphthalenediamine ((A) in the synthesis diagram, manufactured by FUJIFILM Wako Pure Chemical Corporation) and 500 ml of ethanol were placed, and then under ice cooling, 7.9 g (81 mmol) of concentrated sulfuric acid (manufactured by FUJIFILM Wako Pure Chemical Corporation, reagent of special grade) was slowly added dropwise while the internal temperature was maintained at 40° C. or lower. Into the resulting suspension, 56.6 g (500 mmol) of 1-methyl-4-piperidone ((B) in the synthesis diagram, manufactured by FUJIFILM Wako Chemical Corporation) was injected, and then the mixture was allowed to react at an internal temperature of 85° C. for 2 hours. The reaction liquid was cooled to room temperature (25° C.), and to the reaction liquid, 500 ml of ethyl acetate and 324 mL of a 0.5 mol/L aqueous sodium hydroxide solution were slowly added dropwise. After stirring at room temperature for 15 minutes, an aqueous layer was removed. Subsequently, 300 ml of water was added, the mixture was stirred at room temperature for 15 minutes, and an aqueous layer was removed. The same operation was repeated once more. To the obtained organic layer, 50 g of sodium sulfate was added, and the mixture was allowed to stand at room temperature for 15 minutes. After removing sodium sulfate, the solvent was distilled off to obtain an intermediate ((C) in the synthesis diagram) that is a reddish brown solid (yield: 122 g, 95%).

Synthesis of Dye

<Preparation of Diazonium Salt Solution>

Into a 500 ml three-necked flask, 20.4 g (64 mmol) of a hydrochloride of a monoazo compound ((D) in the synthesis diagram), 74 mL of water, and 147 mL of acetic acid (manufactured by FUJIFILM Wako Pure Chemical Corporation, reagent of special grade) were placed, and the mixture was cooled to have an internal temperature of 5° C. To the mixture, 14.8 mL (213 mmol) of a 85% aqueous phosphoric acid solution (manufactured by FUJIFILM Wako Pure Chemical Corporation, reagent of special grade) was carefully added dropwise at an internal temperature of 10° C. or lower, and then an aqueous solution obtained by dissolving 4.9 g (71 mmol) of sodium nitrite (manufactured by FUJIFILM Wako Pure Chemical Corporation, reagent of special grade) in 10 mL of water was slowly added dropwise while the internal temperature was maintained at 0 to 5° C. The mixture was reacted at an internal temperature of 0 to 5° C. for 1 hour, then 0.68 g (7 mmol) of amidosulfuric acid (manufactured by FUJIFILM Wako Pure Chemical Corporation) was carefully added, and the mixture was stirred for 15 minutes.

<Preparation of Dye Precursor>

Separately, in a 1 L three-necked flask, 18.5 g (71 mmol) of the previously prepared intermediate ((C) in the synthesis diagram) was added to 210 mL of acetone (manufactured by FUJIFILM Wako Pure Chemical Corporation, reagent of special grade), and the mixture was cooled to have an internal temperature of 5° C. Next, the previously prepared diazonium salt solution was slowly added dropwise while the internal temperature was maintained at 5 to 10° C., and then the mixture was allowed to react at an internal temperature of 0 to 10° C. for 30 minutes and subsequently react at 15 to 20° C. for 30 minutes. Into the flask, 580 mL of acetone was added dropwise, and the precipitated crystal was filtered by suction filtration and washed with acetone.

The obtained wet cake was subjected to column purification with an ethyl acetate/methanol solvent to obtain a dye precursor ((E) in the synthesis diagram) that is a dark green glossy crystal (yield: 9.6 g, 27%).

Dye Precursor:

$^1$H-NMR (DMSO-$d_6$): 1.83 (brs, 4H), 2.35 (s, 3H), 6.70 (d×2, 2H), 6.83 (s, 1H), 7.42 (t, 1H), 7.58 (m, 2H), 7.78 (d, 1H), 7.82 (m, 2H), 7.96 (d, 1H), 8.05 (d, 3H), 8.15 (d, 1H), 8.21 (d, 1H), 9.04 (d, 1H), 9.09 (d, 1H)

Synthesis of Cationic Dye 1

Into a 500 ml three-necked flask, 25.0 g (45.8 mmol) of the previously prepared dye precursor ((E) in the synthesis diagram) and 250 ml of acetone were placed, and then 10.7 g (68.7 mmol) of iodoethane (manufactured by FUJIFILM Wako Pure Chemical Corporation) was further added dropwise to the obtained solution. Thereafter, the mixture was heated to a temperature of 50° C. and react for 8 hours. After completion of the reaction, the temperature was lowered to room temperature, and filtration was performed. The obtained solid was washed with acetone to obtain a cationic dye 1 ((F) in the synthesis diagram) (yield: 30.0 g, 93%).

Synthesis of Cationic Dye 2

Into a 200 ml three-necked flask, 10.0 g (14.2 mmol) of the previously prepared cationic dye 1 ((F) in the synthesis diagram) and 50 ml of ethyl acetate were placed, and then 50 ml of water in which 5.2 g (28.2 mmol) of potassium hexafluorophosphate (manufactured by FUJIFILM Wako Pure Chemical Corporation) was dissolved was further added to the obtained solution. The obtained reaction liquid was stirred at room temperature for 2 hours, and then an aqueous layer was removed. Then, 50 ml of water was added to the obtained organic layer (ethyl acetate layer), the mixture was stirred for 5 minutes, and an aqueous layer was removed. The same operation was repeated once more, sodium sulfate was added to the obtained organic layer (ethyl acetate layer), and the mixture was allowed to stand for 15 minutes. Next, sodium sulfate was filtered, and the solvent was removed with a rotary evaporator to obtain a cationic dye 2 ((G) in the synthesis diagram) (yield: 5.9 g, 58%). NMR data of cationic dye 1 and cationic dye 2:

$^1$H-NMR (DMSO-$d_6$): 1.30 (t, 3H), 2.20 (brs, 4H), 3.05 (s, 3H), 3.50 (t, 2H), 3.60 (brs, 4H), 6.80 (d×2, 2H), 6.94 (brs, 1H), 7.50 (t, 1H), 7.60 (m, 2H), 7.68 (d, 1H), 7.85 (m, 2H), 7.98 (d, 2H), 8.05 (q, 2H), 8.25 (d, 2H), 9.05 (d, 1H), 9.11 (d, 1H)

Synthesis of Colored Fiber (Example 1)

An acrylic polymer including 49 mass % of a repeating unit derived from acrylonitrile, 50 mass % of a repeating unit derived from vinyl chloride, and 1 mass % of a repeating unit derived from sodium styrenesulfonate was dissolved in acetone to produce a resin solution having a resin concentration of 28.0 mass %.

Next, the previously prepared cationic dye 2 and a red dye (C.I Basic Red 46) were added as colorants to the resin solution so that the contents of the cationic dye 2 and the red dye were 2.5 parts by mass and 0.075 parts by mass, respectively, with respect to 100 parts by mass of the acrylic polymer.

Furthermore, polyglycidyl methacrylate (weight average molecular weight: 12,000) was added in an amount of 0.9 mass % with respect to 100 mass % of the acrylic polymer to produce a spinning dope.

The spinning dope was extruded and coagulated in a coagulation bath of a 40 mass % acetone aqueous solution at 25° C. using a spinning nozzle to form a fiber, and then solvent removal and drawing were performed with hot water at 75° C. Next, the primary drawn yarn having undergone washing with water was immersed in an oil agent bath (containing a fatty acid ester-based oil agent, a polyoxyethylene-based surfactant, and water as main components) into which an oil agent for fibers was introduced, and thus the primary drawn yarn was impregnated with the oil agent for fibers and then subjected to drying, drawing, and heat treatment to obtain an acrylic fiber having a single fiber fineness of about 46 dtex and colored black.

Synthesis of Colored Fiber (Comparative Example 1)

An acrylic polymer including 49 mass % of a repeating unit derived from acrylonitrile, 50 mass % of a repeating unit derived from vinyl chloride, and 1 mass % of a repeating unit derived from sodium styrenesulfonate was dissolved in acetone to produce a resin solution having a resin concentration of 28.0 mass %.

Next, carbon black was added as a colorant to the resin solution in an amount of 2.0 parts by mass with respect to 100 parts by mass of the acrylic polymer.

Furthermore, polyglycidyl methacrylate (weight average molecular weight: 12,000) was added in an amount of 0.9 mass % with respect to 100 mass % of the acrylic polymer to produce a spinning dope.

The spinning dope was extruded and coagulated in a coagulation bath of a 40 mass % acetone aqueous solution at 25° C. using a spinning nozzle to form a fiber, and then solvent removal and drawing were performed with hot water at 75° C. Next, the primary drawn yarn having undergone washing with water was immersed in an oil agent bath (containing a fatty acid ester-based oil agent, a polyoxyethylene-based surfactant, and water as main components) into which an oil agent for fibers was introduced, and thus the primary drawn yarn was impregnated with the oil agent for fibers and then subjected to drying, drawing, and heat treatment to obtain an acrylic fiber having a single fiber fineness of about 46 dtex and colored black.

Synthesis of Colored Fiber (Comparative Example 2)

An acrylic polymer including 49 mass % of a repeating unit derived from acrylonitrile, 50 mass % of a repeating unit derived from vinyl chloride, and 1 mass % of a repeating unit derived from sodium styrenesulfonate was dissolved in acetone to produce a resin solution having a resin concentration of 28.0 mass %.

Next, a black dye (Sudan Black B) and a red dye (C.I Basic Red 46) were added as colorants to the resin solution so that the contents of the black dye and the red dye were 2.5 parts by mass and 0.075 parts by mass, respectively, with respect to 100 parts by mass of the acrylic polymer.

Furthermore, polyglycidyl methacrylate (weight average molecular weight: 12, 000) was added in an amount of 0.9 mass % with respect to 100 mass % of the acrylic polymer to produce a spinning dope.

The spinning dope was extruded and coagulated in a coagulation bath of a 40 mass % acetone aqueous solution at 25° C. using a spinning nozzle to form a fiber, and then solvent removal and drawing were performed with hot water at 75° C. Next, the primary drawn yarn having undergone washing with water was immersed in an oil agent bath (containing a fatty acid ester-based oil agent, a polyoxyethylene-based surfactant, and water as main components) into which an oil agent for fibers was introduced, and thus the primary drawn yarn was impregnated with the oil agent for fibers and then subjected to drying, drawing, and heat treatment to obtain an acrylic fiber having a single fiber fineness of about 46 dtex and colored black.

Evaluation Results

The obtained colored fibers of Example 1 and Comparative Examples 1 to 2 were evaluated for the heat generation suppression property and the fastness in hot water at 90° C.

Evaluation Method for Heat Generation Suppression Property

The colored fiber of each of Example 1 and Comparative Examples 1 to 2 was formed into a hair bundle-like sample having a length of 30 mm, a width of 30 mm, and a thickness of 10 mm. Next, the sample was set in a constant-temperature constant-humidity chamber adjusted to a temperature of 32° C. and a humidity of 60%, pseudo sunlight (light source: an artificial solar illumination lamp capable of irradiating a surface of a test piece at a spectral match specified in JIS C 8904-9 of grade B or higher and an irradiance of 800±100 $W/m^2$) was set at a distance of 200 mm from the sample, the sample was exposed to the pseudo sunlight for 20 minutes, and then the surface temperature of the colored fiber was measured with a thermocouple.

Evaluation Method for Fastness in Hot Water at 90° C.

When 2 g of the colored fiber of each of Example 1 and Comparative Examples 1 to 2 was immersed in 10 g of hot water at 90° C. in a container, the hue of the hot water was visually observed to determine the amount of the colorant eluted from the colored fiber. From the observed hue, the fastness was evaluated in accordance with the following criteria.

(Evaluation Criteria)

A: The hue is colorless and transparent or light, and the fastness is excellent.

B: The hue is dark, and the fastness is poor.

In Example 1 and Comparative Example 2, the difference in surface temperature of the colored fiber between before and after the exposure to pseudo sunlight was 30° C. (increase of 30° C.), whereas in Comparative Example 1, the difference in surface temperature of the colored fiber between before and after the exposure to pseudo sunlight was 42° C. (increase of 42° C.).

In Example 1 and Comparative Example 1, when the colored fiber was immersed in hot water of 90° C., the amount of the colorant eluted from the colored fiber was small and the fastness was good, whereas in Comparative Example 2, when the colored fiber was immersed in hot water of 90° C., the amount of the colorant eluted from the colored fiber was large, and the fastness was poor.

Although the disclosure has been described with respect to only a limited number of embodiments, those skilled in the art, having benefit of this disclosure, will appreciate that various other embodiments may be devised without departing from the scope of the present disclosure. Accordingly, the scope of the invention should be limited only by the attached claims.

The inventiopn claimed is:

1. A colored fiber comprising a fiber and a compound expressed by Formula (1):

(1)

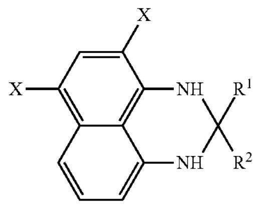

wherein $R^1$ and $R^2$ each independently represent a hydrogen atom or a substituent, $R^1$ and $R^2$ are optionally bonded to each other to form a ring, and of two Xs, one X represents a hydrogen atom and another X represents a group expressed by Formula (1a):

(1a)

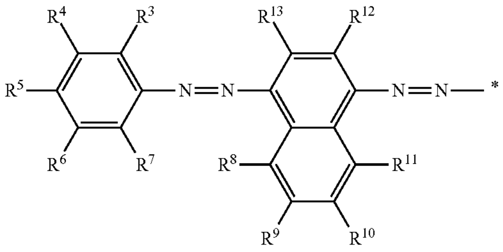

wherein $R^3$ to $R^{13}$ each independently represent a hydrogen atom or a substituent, two adjacent groups among $R^3$ to $R^{13}$ are optionally bonded to each other to form a ring, and * represents a bonding position, the compound expressed by Formula (1) satisfying at least one of Requirements 1 to 3 described below:

Requirement 1: at least one of $R^1$ to $R^{13}$ represents a substituent comprising a partial structure expressed by Formula (1b):

$$*—X_1^+Y^- \quad \text{Formula (1b):}$$

wherein $X_1^+$ represents a cationic group, $Y^-$ represents an anionic counterion, and * represents a bonding position, Requirement 2: $R^1$ and $R^2$ are bonded to each other to form a ring, the ring comprises a partial structure of $X_2^+$ $(Y^-)$, $X_2^+$ represents a cationic atom constituting a ring member atom of the ring, and $Y^-$ represents an anionic counterion, and Requirement 3: two adjacent groups among $R^3$ to $R^{13}$ are bonded to each other to form a ring, the ring comprises a partial structure of $X_3^+$ $(Y^-)$, $X_3^+$ represents a cationic atom constituting a ring member atom of the ring, and $Y^-$ represents an anionic counterion.

2. The colored fiber according to claim 1, wherein the fiber is an acrylic fiber comprising an acrylic polymer.

3. The colored fiber according to claim 2, wherein the acrylic polymer comprises:

a repeating unit X derived from an acrylonitrile monomer;

one or more kinds of repeating units Y selected from the group consisting of repeating units derived from a vinylidene chloride monomer and repeating units derived from a vinyl chloride monomer; and a repeating unit Z derived from a sulfonate group-containing vinyl monomer, wherein a content of the repeating unit X is 29.5 to 79.5 mass % with respect to a total mass of the acrylic polymer, wherein a content of the repeating units Y is 20 to 70 mass % with respect to the total mass of the acrylic polymer, and wherein a content of the repeating unit Z is 0.5 to 5 mass % with respect to the total mass of the acrylic polymer.

4. The colored fiber according to claim 1, wherein in Formula (1), at least one of $R^1$ or $R^2$ represents a substituent including a partial structure expressed by Formula (1b), or $R^1$ and $R^2$ are bonded to each other to form a ring and the ring comprises a partial structure of $X_2^+$ $(Y^-)$.

5. The colored fiber according to claim 1, wherein the anionic counterion of $Y^-$ is one selected from the group consisting of sulfonimide ions, a hexafluorophosphate ion, an iodide ion, a saccharin ion, and a tosylate ion.

6. A method for manufacturing the colored fiber according to claim 1, the method comprising a step of wet-spinning a spinning dope comprising a polymer included in the fiber and the compound expressed by Formula (1).

7. A method for manufacturing the colored fiber according to claim 1, the method comprising a step of dyeing the fiber using an aqueous solution comprising the compound expressed by Formula (1).

8. A fiber product comprising the colored fiber according to claim 1.

9. The fiber product according to claim 8, wherein the fiber product is a head decoration product.

10. The fiber product according to claim 9, wherein the head decoration product is selected from the group consisting of fiber bundles for hair, weaving products, wigs, braids, toupees, hair extensions, and hair accessories.

11. The colored fiber according to claim 2, wherein in Formula (1), at least one of $R^1$ or $R^2$ represents a substituent including a partial structure expressed by Formula (1b), or $R^1$ and $R^2$ are bonded to each other to form a ring and the ring comprises a partial structure of $X_2^+$ $(Y^-)$.

12. The colored fiber according to claim 2, wherein the anionic counterion of $Y^-$ is one selected from the group consisting of sulfonimide ions, a hexafluorophosphate ion, an iodide ion, a saccharin ion, and a tosylate ion.

13. A method for manufacturing the colored fiber according to claim 2, the method comprising a step of wet-spinning a spinning dope comprising a polymer included in the fiber and the compound expressed by Formula (1).

14. A method for manufacturing the colored fiber according to claim 2, the method comprising a step of dyeing the fiber using an aqueous solution comprising the compound expressed by Formula (1).

15. A fiber product comprising the colored fiber according to claim 2.

16. The fiber product according to claim 15, wherein the fiber product is a head decoration product.

17. The fiber product according to claim 16, wherein the head decoration product is selected from the group consisting of fiber bundles for hair, weaving products, wigs, braids, toupees, hair extensions, and hair accessories.

18. The colored fiber according to claim 3, wherein in Formula (1), at least one of $R^1$ or $R^2$ represents a substituent including a partial structure expressed by Formula (1b), or $R^1$ and $R^2$ are bonded to each other to form a ring and the ring comprises a partial structure of $X_2^+$ $(Y^-)$.

19. The colored fiber according to claim 3, wherein the anionic counterion of $Y^-$ is one selected from the group consisting of sulfonimide ions, a hexafluorophosphate ion, an iodide ion, a saccharin ion, and a tosylate ion.

20. A method for manufacturing the colored fiber according to claim 3, the method comprising a step of wet-spinning a spinning dope comprising a polymer included in the fiber and the compound expressed by Formula (1).

* * * * *